US009693829B2

(12) United States Patent
Shi et al.

(10) Patent No.: US 9,693,829 B2
(45) Date of Patent: Jul. 4, 2017

(54) MICROSCOPIC SURGERY SYSTEM AND NAVIGATION METHOD GUIDED BY OPTICAL COHERENCE TOMOGRAPHY (OCT) AND AUTOMATED OCT IMAGING FIELD CALIBRATION

(71) Applicant: The Institute of Optics and Electronics, The Chinese Academy of Sciences, Sichuan (CN)

(72) Inventors: Guohua Shi, Sichuan (CN); Yi He, Sichuan (CN); Xiqi Li, Sichuan (CN); Zhibin Wang, Sichuan (CN); Yudong Zhang, Sichuan (CN)

(73) Assignee: The Institute of Optics and Electronics, the Chinese Academy of Sciences, Chengdu (CN)

( * ) Notice: Subject to any disclaimer, the term of this patent is extended or adjusted under 35 U.S.C. 154(b) by 183 days.

(21) Appl. No.: 14/614,703

(22) Filed: Feb. 5, 2015

(65) Prior Publication Data

US 2015/0272697 A1 Oct. 1, 2015

(30) Foreign Application Priority Data

Mar. 27, 2014 (CN) .......................... 2014 1 0117985

(51) Int. Cl.
*A61B 19/00* (2006.01)
*A61B 5/00* (2006.01)
(Continued)

(52) U.S. Cl.
CPC ........ *A61B 19/5244* (2013.01); *A61B 5/0066* (2013.01); *A61B 90/20* (2016.02);
(Continued)

(58) Field of Classification Search
CPC ........... A61B 3/102; A61B 3/13–3/135; A61B 5/0066; A61B 2560/0223
See application file for complete search history.

(56) References Cited

U.S. PATENT DOCUMENTS

| 2012/0092615 | A1* | 4/2012 | Izatt | ........................ | A61B 3/102 |
| | | | | | 351/206 |
| 2012/0184846 | A1* | 7/2012 | Izatt | ................... | G02B 21/0012 |
| | | | | | 600/425 |

(Continued)

*Primary Examiner* — Serkan Akar
(74) *Attorney, Agent, or Firm* — Knobbe, Martens, Olson & Bear, LLP (57) ABSTRACT

Provided are a microscopic surgery system and a navigation method guided by optical coherence tomography. The microscopic surgery system may include: an object lens; a surgical microscope unit configured to perform two-dimensional imaging on an area to operate on via the object lens; an optical coherence tomography unit configured to perform two-dimensional tomography imaging on the area via the object lens, with an imaging field calibrated according to that of the surgical microscope unit; a processor configured to obtain navigation information based on the two-dimensional imaging by the surgical microscope unit and the two-dimensional tomography imaging by the optical coherence tomography unit, the navigation information comprising positional information of a body part to operate on and a surgical instrument for operating on the body part; and an output unit configured to output the navigation information to guide the surgical instrument to the body part.

9 Claims, 6 Drawing Sheets (51) Int. Cl.
*A61B 90/20* (2016.01)
*A61B 90/00* (2016.01)

(52) U.S. Cl.
CPC . *A61B 2090/3735* (2016.02); *A61B 2090/395* (2016.02); *A61B 2560/0223* (2013.01)

(56) References Cited

U.S. PATENT DOCUMENTS

2013/0103014 A1* 4/2013 Gooding ................ A61B 3/102
606/6
2015/0141972 A1* 5/2015 Woodley ................ A61B 3/102
606/5

* cited by examiner

MICROSCOPIC SURGERY SYSTEM AND NAVIGATION METHOD GUIDED BY OPTICAL COHERENCE TOMOGRAPHY (OCT) AND AUTOMATED OCT IMAGING FIELD CALIBRATION

TECHNICAL FIELD

The present disclosure relates to imaging and image processing in microscopic surgery, and in particular, to a microscopic surgery system and a navigation method guided by Optical Coherence Tomography (OCT).

BACKGROUND

In modern surgery, it is desirable to accurately locate a target spot to operate on while reducing physical injuries of patients as much as possible, to achieve minimally invasive surgery, so as to overcome defects such as a large surgical wound, a long recovery phase or the like due to rough open surgery in the past, and to minimize the physical and psychological injuries of the patients. Image-guided interventional surgery can accurately locate a target spot to operate on, achieve features such as monitoring and navigation or the like in the process of surgery, and has advantages such as a small wound, a short recovery phase, a good curative effect or the like. Therefore, the interventional surgery is an important development direction for the modern surgery, and presents a trend to gradually replace the conventional open surgery.

Most of operations are directed to deep tissues. Conventional methods are done by cutting surface tissues open, and then performing relevant surgical treatment on the deep tissues. Therefore, in order to achieve image-guided operations to ensure safe and effective development of the operations, it is desirable to incorporate imageology technology for achieving three-dimensional imaging of the deep tissues. Currently, three three-dimensional imaging techniques, i.e., ultrasonics, CT and magnetic resonance imaging, have been successfully incorporated into surgical systems, to achieve image-guided surgical navigation, and have been successfully applied to clinic surgery for breast, abdomen, head or the like.

However, those three imaging approaches have low resolutions. Specifically, resolutions of clinical instruments using these approaches are in an order of millimeters. Therefore, only navigation for operations without high demands on fineness can be achieved. Further, current microscopic surgery based on optical surgical microscopes, for example, ophthalmic surgery, neurosurgery or the like,is limited to two-dimensional (for example, in an x-y plane) imaging. Although the optical surgical microscope used in the surgery has a resolution up to an order of micrometers, there has been no three-dimensional imaging (x-y-z 3D imaging) technology with a matched resolution to cooperate therewith. In addition, as an area to operate on in the microscopic surgery is very small, factors such as deformations due to vibration and tissue cutting in the operation will directly cause an overall deformation of the area to operate on. Therefore, non-real time imaging techniques,such as magnetic resonance and CT, are not suitable for navigation in the microscopic surgery. Due to the above problems, image navigation for operations has not been achieved so far in the microscopic surgery.

SUMMARY

The present disclosure aims to provide, among others, a microscopic surgery system and a microscopic surgery navigation method guided by OCT, by which it is possible to achieve navigation in microscopic surgery based on guidance by two-dimensional and three-dimensional images of the OCT by cooperating with a surgical microscope.

According to an aspect of the present disclosure, there is provided a microscopic surgery system, comprising: an object lens; a surgical microscope unit configured to perform two-dimensional imaging on an area to operate on via the object lens; an OCT unit configured to perform two-dimensional tomography imaging on the area to operate on via the object lens, wherein an imaging field of the OCT unit is calibrated according to an imaging field of the surgical microscope unit; a processor configured to obtain navigation information based on the two-dimensional imaging by the surgical microscope unit and the two-dimensional tomography imaging by the OCT unit, the navigation information comprising positional information of a body part to operate on and a surgical instrument for operating on the body part; and an output unit configured to output the navigation information to guide the surgical instrument to the body part.

The object lens may comprise a microscopic object lens. The surgical microscope unit may be configured to perform imaging via a paraxial area of the object lens, and the OCT unit may be configured to perform imaging via an on-axis area of the object lens.

The navigation information may comprise at least one of a two-dimensional image from the surgical microscope unit, a two-dimensional tomography image of the OCT unit, or a three-dimensional image derived from the two-dimensional tomography image. In this case, the output unit may comprise a display unit configured to display the navigation information. The processor may be configured to highlight the body part to operate on and/or the surgical instrument on the displayed two-dimensional image and/or three-dimensional image.

According to another aspect of the present disclosure, there is provided a microscopic surgery navigation method, comprising: calibrating an imaging field of an OCT unit according to an imaging field of a surgical microscope unit; performing, by the surgical microscope unit, two-dimensional imaging on an area to operate on via an object lens, and performing, by the OCT unit, two-dimensional tomography imaging on the area to operate on via the object lens; obtaining navigation information based on results of the imaging, the navigation information comprising positional information of a body part to operate on and a surgical instrument for operating on the body part; and outputting the navigation information to guide the surgical instrument to the body part.

Calibrating an imaging field of an OCT unit may comprise: establishing a unified coordinate system,with a center of the imaging field of the surgical microscope unit as an origin and optical scanning lines of the OCT unit as x, y, and z axes; and recording positions, in the coordinate system, of the x and y scanning lines of the OCT driven unit under different scanning voltages and establishing a correspondence relationship between different driving voltages and scanning positions.

The navigation information may comprise at least one of a two-dimensional image from the surgical microscope unit, a two-dimensional tomography image from the OCT unit, and a three-dimensional image derived from the two-dimensional tomography image. In this case, outputting the navigation information may comprise displaying the navigation information. The method may further comprise highlighting the body part to operate on and/or the surgical instrument on the displayed two-dimensional image and/or three-dimensional image.

The method may further comprise performing y-z plane tomography imaging and x-z plane tomography imaging at a fixed time interval, and obtaining a current position of the surgical instrument based on a y-z tomography image and an x-z tomography image in two consecutive frames.

According to embodiments of the present disclosure, based on the OCT technology, the guiding image can have a resolution in an order of micrometers. Therefore, it is possible to overcome defects in resolution of the existing imaging techniques such as ultrasonics, CT and magnetic resonance, and to match the resolution required by the optical microscopic surgery, thereby achieving navigation of the microscopic surgery guided by OCT.

According to embodiments of the present disclosure, optics is used as an imaging medium for the guiding image, unlike the imaging techniques, such as ultrasonics and magnetic resonance, where additional imaging consumptive materials (such as ultrasonic emulsion and isotope) are needed, thereby reducing additional physical injuries of patients due to the image navigation.

According to embodiments of the present disclosure, real-time imaging can be achieved on a body part of a patient in three planes, i.e., x-z, y-z and x-y planes, and a 3-Dimensional (3D) coordinate distribution of the position to operate on can be quickly determined. Real-time navigation can be achieved by 3D imaging at several frames per second, thereby effectively reducing various problems due to deformation of the position to operate on.

BRIEF DESCRIPTION OF THE DRAWINGS

The above and other objects, features, and advantages of the present disclosure will become more apparent from following descriptions of embodiments thereof with reference to attached drawings, in which.

DETAILED DESCRIPTION

Hereinafter, descriptions are given with reference to embodiments shown in the attached drawings. However, it is to be understood that these descriptions are illustrative and not intended to limit the present disclosure. Further, in the following, known structures and technologies are not described to avoid obscuring the present disclosure unnecessarily.

Figure 1:
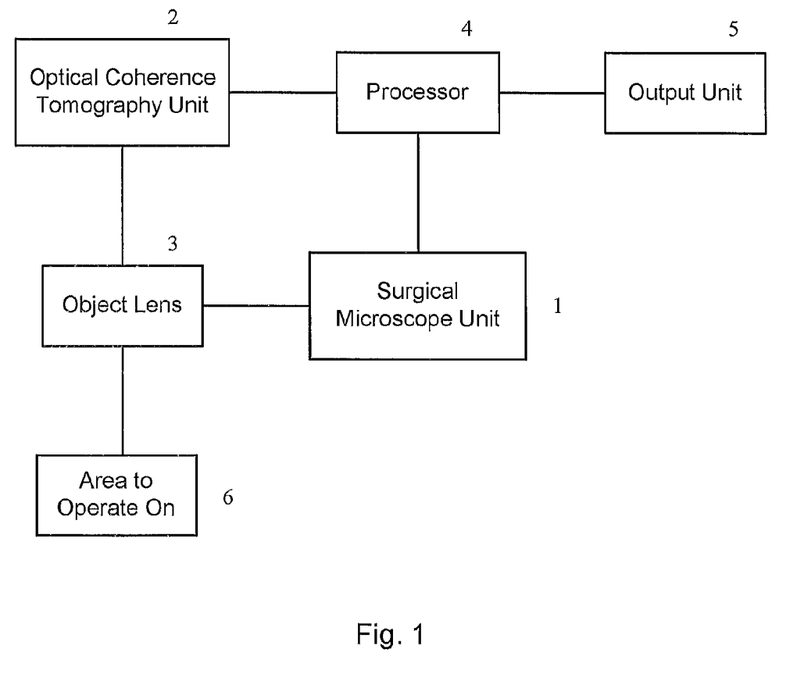
FIG. 1 is a schematic block diagram illustrating a configuration of a microscopic surgery system according to an embodiment of the present disclosure.

FIG. 1 is a block diagram illustrating a configuration of a microscopic surgery system according to an embodiment of the present disclosure.

As shown in FIG. 1, the microscopic surgery system may include a surgical microscope unit 1, an OCT unit 2, an object lens 3, a processor 4 and an output unit 5.

The surgical microscope unit 1 is configured to perform large-field two-dimensional (for example, in an x-y plane) imaging on an area of a patient to operate on. An imaging field of the surgical microscope unit 1 may be used to calibrate an imaging field of the OCT unit 2. For example, an illuminating beam of the surgical microscope unit 1 may be transmitted through the object lens 3 to the area to operate on 6, and then reflected by the area to operate onto propagate back to the surgical microscope unit 1 through the object lens 3. An operator (for example, a surgeon) may observe a large-field two-dimensional image of the area to operate on with his eyes at an exit pupil position of the surgical microscope unit 1. On the other hand, the surgical microscope unit 1 may convert a detected imaging signal into an electrical signal, and output it to the processor 4 for processing.

The OCT unit 2 is configured to perform two-dimensional tomography (for example, in an x-z plane) imaging on the area of the patient to operate on. For example, an imaging beam of the OCT unit 2 may be transmitted through the object lens 3 to the area to operate on 6, and then reflected by the area to operate on 6 to propagate back to the OCT unit 2 through the object lens 3. The OCT unit 2 may convert a detected (interference) signal into an electrical signal, and output it to the processor 4 for processing.

As described above, the imaging field of the OCT unit 2 may be calibrated according to the imaging field of the surgical microscope unit 1. For example, the imaging field of the OCT unit 2 may be calibrated at a center of the imaging field of the surgical microscope unit 1 with reference to the large-field two-dimensional (for example, x-y plane) image of the area of the patient to operate on obtained by the surgical microscope unit 1.

In this embodiment, the object lens 3 may be shared by the surgical microscope unit 1 and the OCT unit 2, to propagate and image the beams of the surgical microscope unit 1 and the OCT unit 2 at the same time. The object lens 3 may comprise a microscopic object lens.

The processor 4 is configured to process electrical signals including imaging information outputted from the surgical microscope unit 1 and the OCT unit 2 in a variety of ways, for example, converting the electrical signals into images for output by the output unit 5. Specifically, the processor 4 may collect the electrical signals outputted from the surgical microscope unit 1 to obtain a large-field two-dimensional (for example, x-y plane) image of the area to operate on. In addition, the processor may reconstruct the electrical signals outputted from the OCT unit 2 to obtain a two-dimensional tomography (for example, x-z plane) image of the area to operate on, and may further obtain a three-dimensional (x-y-z) image by concatenating a sequence of two-dimensional tomography images using an algorithm.

In addition, the processor 4 may obtain navigation information based on the two-dimensional imaging by the surgical microscope unit 1 and the two-dimensional tomography imaging by the OCT unit 2. Here, the navigation information may refer to positional information of a body part to operate on and positional information of a surgical instrument (for example, a surgical knife) for operating on the body part. For example, the navigation information may comprise accurate positional information of the body part to operate on and accurate positional information of the surgical instrument, or relative positional information of the surgical instrument with respect to the body part. The processor 4 may be implemented in an analog control circuit or a digital computer.

The navigation information may comprise intuitive image information, for example, the two-dimensional image obtained by the surgical microscope unit 1 and/or the two-dimensional tomography image and/or three-dimensional image obtained by the OCT unit 2, on which the body part to operate on and the surgical instrument are intuitionally displayed. The operator may move the surgical instrument to the body part to operate on according to the intuitive display, especially, the display of the three-dimensional image. The navigation information may further comprise position coordinates of the body part to operate on and position coordinates of the surgical instrument. For example, these position coordinates may be obtained by the processor 4 performing image recognition on the image, and/or may be inputted by the operator to the processor 4, as described further in detail below. In addition, the navigation information may further comprise voice information, for example, voice guiding the operator to move the surgical instrument (for example, "forward", "backward", "leftward", "rightward", "downward", "upward" etc.). Such voice information may be obtained by the processor 4 based on the position of the body part to operate on and the position of the surgical instrument.

The output unit 5 may be configured to output the navigation information to the outside in a form of video and/or audio. For example, the output unit 5 may comprise a display device, such as a Liquid Crystal Display (LCD) device, a Light Emitting Diode (LED) display device, and an Organic Light Emitting Diode (OLED) display device. In this case, the display device may display the navigation information thereon, for example, the accurate position of the body part to operate on and the accurate position of the surgical instrument, thereby guiding the surgical instrument to the body part to operate on. In addition, the display device may also display at least one of the large-field two-dimensional (for example, x-y plane) image, the two-dimensional (for example, x-z plane) tomography image and the three-dimensional image of the area to operate on, and may mark the body part to operate on and the surgical instrument in the displayed image. For example, the mark may comprise highlighting (for example, displaying in highlight or in other colors), addition of indicators (for example, cross or star), or the like.

In addition, the output unit 5 may additionally or alternatively comprise an audio output device, for example, a speaker. The audio output device may output audio such as "forward", "backward", "leftward", "rightward", "downward", and "upward" based on the navigation information, to guide the surgical instrument to the body part to operate on.

According to an embodiment of the present disclosure, the system may further comprise an input device, for example, a mouse, a keyboard, or the like, to input commands and data to the system, in particular, the processor 4. For example, the input device may comprise a touch panel. The touch panel may be incorporated into the output unit 5 in a form of display device (thereby enabling the output unit 5 to be implemented in a form of touch screen).

The operator may touch the body part to operate on in the image displayed on the touch screen, for example, the large-field two-dimensional (for example, x-y plane) image obtained by the surgical microscope unit 1 and the two-dimensional (for example, x-z plane) tomography image obtained by the OCT unit 2, so as to input the positional information of the body part to operate on to the processor 4. In an example, the operator may touch, in the large-field two-dimensional (for example, x-y plane) image of the surgical microscope unit 1, a position of the body part to operate on the two-dimensional plane, for example (x1, y1). The processor 4 may call, based on the touch, the two-dimensional tomography image of the OCT unit 2 at this position, for example, a two-dimensional tomography image on an x1-z plane, and display the two-dimensional tomography image on the output unit 5. The operator may specify a depth z1 of the body part to operate on at the position (x1,y1) by touching the two-dimensional tomography image, so as to input three-dimensional coordinates (x1,y1,z1) of the body part to operate on.

In the present embodiment, the body part to operate on is described as a single position. However, it is to be noted that the body part to operate on is not limited to a single point, and instead may comprise a certain area. The operator may specify the position of the area. Alternatively, the operator may specify positions of one or more points in the area.

The processor 4 may convert the positional information of the body part to operate on into a unified coordinate system based on the touch input from the operator. In addition, the processor 4 may highlight, according to the positional information of the body part to operate on, the body part to operate on the two-dimensional image and/or three-dimensional image displayed on the output unit 5 (for example, in different colors or in highlight).

According to a further embodiment of the present disclosure, the processor 4 may obtain the positional information of the body part to operate on by performing image recognition on the large-field two-dimensional (for example, x-y plane) image obtained by the surgical microscope unit 1 and the two-dimensional (for example, x-z plane) tomography image obtained by the OCT unit 2. For example, the body part to operate on may be displayed differently from surrounding tissues in the image due to disease, and thus can be easily identified. Alternatively, a particular mark substance (such as a substance which tends to absorb light or reflect light) may be injected into the body part to operate on before the surgery, to facilitate identifying the body part to operate on subsequently.

According to another embodiment of the present disclosure, the processor 4 may obtain the positional information of the surgical instrument by performing image recognition on the large-field two-dimensional (for example, x-y plane) image obtained by the surgical microscope unit 1 and the two-dimensional (for example, x-z plane) tomography image obtained by the OCT unit 2. For example, the surgical instrument is generally made of metal, and thus has different optical properties from human tissues. Therefore, the surgical instrument can be easily identified in the image. Alternatively, a particular structure or pattern may be manufactured or additionally added on the surgical instrument, for convenience of identification. In addition, the processor 4 may also highlight, based on the positional information of the surgical instrument, the surgical instrument on the two-dimensional image and/or three-dimensional image displayed on the output unit 5 (for example, in different colors or in highlight).

Figure 2:
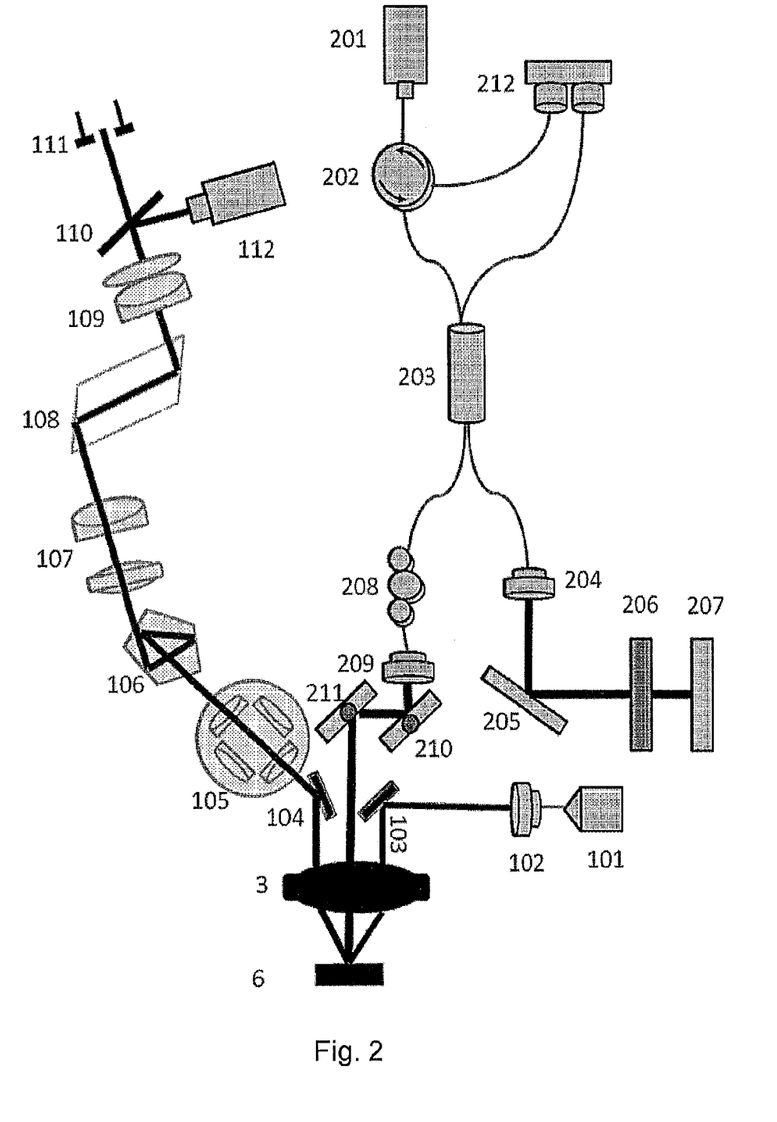
FIG. 2 is a detailed view illustrating a structure of a microscopic surgery system according to an embodiment of the present disclosure.

FIG. 2 is a detailed view illustrating a structure of a microscopic surgery system according to an embodiment of the present disclosure.

As shown in FIG. 2, in a surgical microscope unit (for example, the surgical microscope unit 1 described with reference to FIG. 1), divergent beams emitted by an illumination source 101 are collimated by a collimator lens 102 into parallel beams, and then reflected by a reflector 103. The reflected beams are focused by a paraxial area of an object lens 3 to illuminate an area to operate on 6. The area to operate on 6 may reflect the incident light, and the reflected light carrying light intensity information of the area to operate on is transmitted through the paraxial area of the object lens 3, and then reflected by a reflector 104 to a zooming object lens 105. The zooming object lens 105 is a combination of object lenses with different focal lengths, and may achieve microscopic imaging of the area to operate on in different multiplication factors. The imaging beams are focused and then emitted by the zooming object lens 105, reflected by a roof prism 106 for even times, and then propagate through a relay lens 107. Then, reverse imaging and light path folding are performed by a reserve image prism 108 on the imaging beams, which are then focused by an ocular lens 109 to a beam splitter 110 for beam splitting. One part of the beams enters human's eyes 111, and thus a viewer may observe the body part to operate on directly with his eyes; and the other part of the beams arrives at a planar array detector 112 for detection of a light intensity signal.

The planar array detector 112 converts the received imaging light intensity signal into an electrical signal, and outputs the electrical signal to a processor (for example, the processor 4 described with reference to FIG. 1) for further processing. For example, the processor may reconstruct the electrical signal into an image signal, and may output the image signal to an output unit (for example, the output unit 5 described with reference to FIG. 1) for output.

In an OCT unit 2 (for example, the OCT unit 2 described with reference to FIG. 1), beams emitted by a frequency sweep laser 201 is emitted through a circulator 202, and is divided into two paths by a coupler 203. One path is a reference arm. In the reference arm, reference beams emitted from the coupler 203 are collimated by a fiber collimator 204 into parallel beams, and then pass through a reflector 205 and a neutral filter 206 to arrive at and thus reflected by a reflector 207. The reflected reference beams propagate back to the coupler 203 through the neutral filter 206, the reflector 205 and the fiber collimator 204. The other path is referred to as a sampling arm. In the sampling arm, sampling beams emitted from the coupler 203 are modulated and then emitted by a polarization controller 208, and then collimated by a collimator 209 into parallel beams, which are scanned and emitted by an x-axis scanning oscillator mirror 210 and a y-axis scanning oscillator mirror 211, and then focused to the area to operate on 6 by an on-axis area of the object lens 3. The area to operate on 6 may reflect the sampling beams. The reflected beams carrying light intensity information of the body part to operate on 6 are transmitted through the on-axis area of the object lens 3, and then propagate back to the coupler 203 through the y-axis scanning oscillator mirror 211, the x-axis scanning oscillator mirror 210, the collimator 209 and the polarization controller 208. The reference beams reflected from the reference arm and the sampling beams reflected from the sampling arm are coupled by interference, and then emitted from the coupler 203. One part of the emitted beams enters the circulator 202 and then emitted to a balance detector 212, and the other part of the emitted beams enters directly the balance detector 212. The balance detector 212 performs balance detection on the interference signal.

The balance detector 212 converts the received interference signal into an electrical signal, and outputs the electrical signal to a processor (for example, the processor 4 described with reference to FIG. 1) for further processing. For example, the processor may reconstruct the electrical signal into a tomography image signal of the body part to operate on, and may output the image signal to an output unit (for example, the output unit 5 described with reference to FIG. 1) for output.

Although FIG. 2 illustrates a specific configuration of the surgical microscope unit and the OCT unit, the present disclosure is not limited thereto. Those skilled in the art can contemplate other different configurations of the surgical microscope unit and the OCT unit. The optical parts illustrated in FIG. 2 are merely illustrative, and those skilled in the art can provide/substitute/remove some optical parts for particular purposes. For example, for the purpose of configuration of a light path, one or more reflectors, prisms, or the like may be added/removed.

Figure 3:
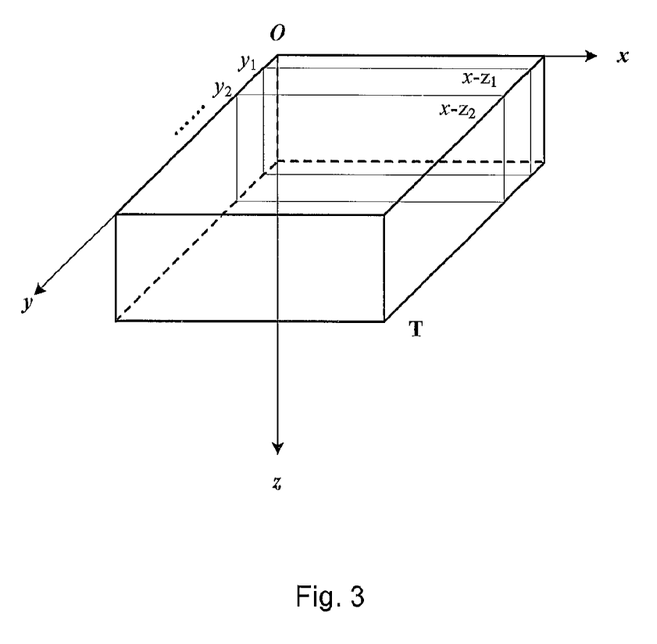
FIG. 3 is a simplified diagram illustrating a basic principle of OCT.

FIG. 3 is a simplified diagram illustrating a basic principle of OCT.

As shown in FIG. 3, a coordinate system x-y-z may be established based on scanning lines of the OCT. For example, scanning may be performed in two directions (x,y) for the OCT, and information about a depth (z) may be obtained during scanning. FIG. 3 also illustrates an object T to be scanned (for example, tissues needed to operate on). It is to be noted that the object T is shown in a shape of hexahedron merely for convenience of illustration. In addition, a position of the object in the coordinate system x-y-z established above is not limited to that shown in the figure, and instead may be any position.

In an example, when the y-scanning line of the OCT is fixed (for example, at a coordinate such as $y_1$ or $y_2$) while the scanning is performed in the x direction, an x-z (for example, x-$z_1$ or x-$z_2$) plane tomography image may be obtained. A series of two-dimensional (x-z plane) images may be obtained by obtaining x-z plane tomography images at different y coordinates. A three-dimensional (x-y-z) image of the object T may be obtained by concatenating these two-dimensional images. There are various ways in the art to derive a three-dimensional stereo image from two-dimensional tomography images.

Similarly, y-z plane tomography images may also obtained through scanning.

Figure 4:
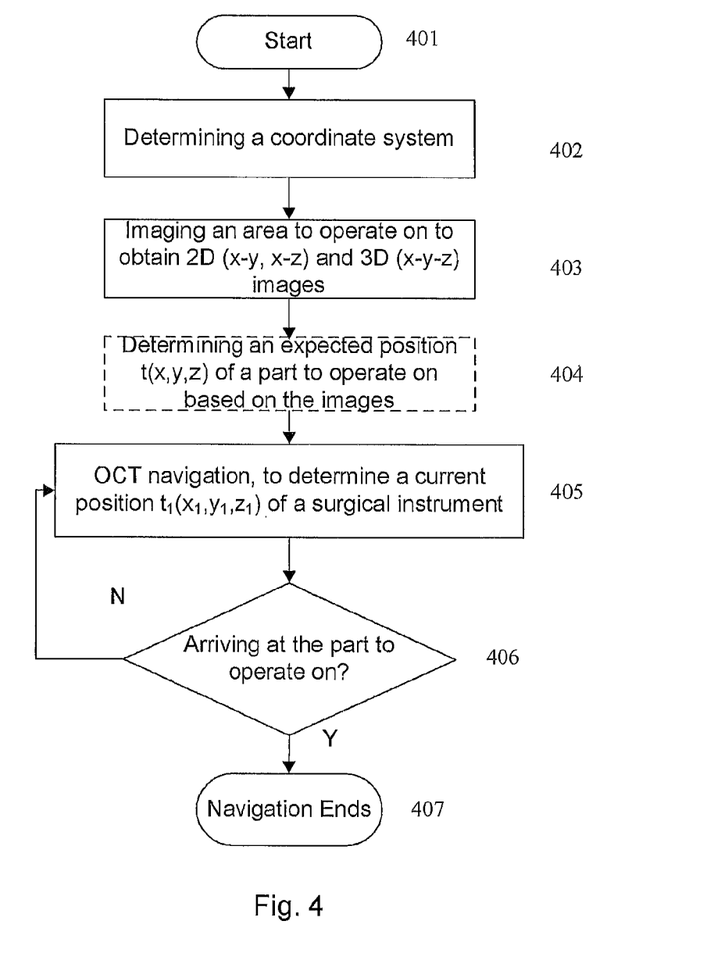
FIG. 4 is a flowchart illustrating a microscopic surgery navigation method according to an embodiment of the present disclosure.
Figure 5:
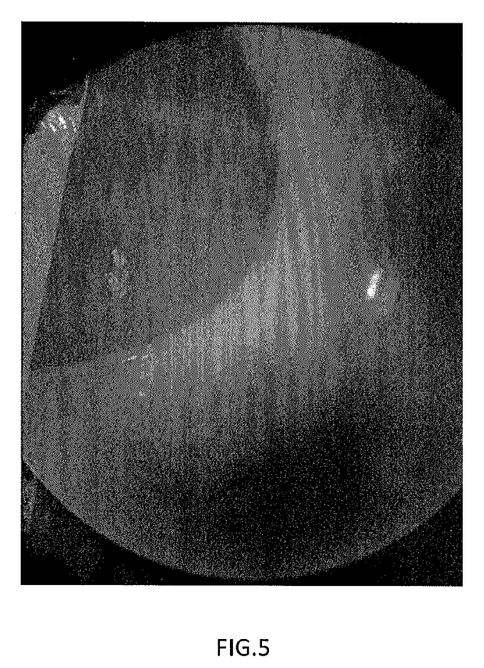
FIG. 5 is a diagram illustrating imaging effect for highlighting the body part (e.g., porcine eye) to operate on the displayed two-dimensional image according to an embodiment of the present disclosure.
Figure 6:
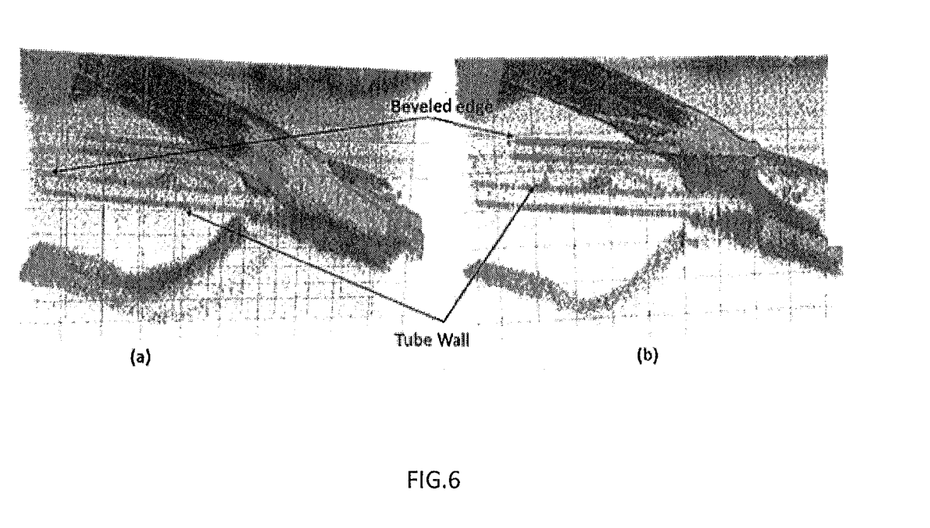
FIG. 6 is a diagram illustrating imaging effect for highlighting the surgical instrument (e.g., Ahmed drainage tube) on the displayed two-dimensional image and/or three-dimensional image according to an embodiment of the present disclosure.

FIG. 4 is a flowchart illustrating a microscopic surgery navigation method according to an embodiment of the present disclosure. This method may be performed by, for example, the microscopic surgery system described with reference to FIG. 1 and/or FIG. 2 above.

The method starts at 401. For example, a doctor and a patient are ready, and the microscopic surgery system is turned on.

Then, the method proceeds to 402. At 402, a unified coordinate system for a surgical microscope unit and an OCT unit may be determined. For example, as described above, an imaging field of the OCT unit may be calibrated based on a center of an imaging field of the surgical microscope unit.

Specifically, a center of large-field imaging by the surgical microscope unit with respect to an area to operate on may be used as an origin of the coordinate system, and optical scanning lines of the OCT unit may be used as x, y, z coordinate axes (reference may be made to FIG. 3), so as to form the unified coordinate system.

An x-y scanning field of the OCT unit may use the center of the imaging field of the surgical microscope unit as a center, to record positions of x-y scanning lines in the coordinate system under different scanning voltages, so as to establish a correspondence relationship between different driving voltages and scanning positions, and store the correspondence relationship in a storage (not shown). For example, the correspondence relationship may be stored in a form of LookUp Table (LUT). The LUT may record a correspondence relationship between specific (x,y) scanning voltages and positions of corresponding scanning lines in the coordinate system.

Then, the method proceeds to 403. At 403, the area to operate on is imaged, to obtain two-dimensional images, for example, a large-field two-dimensional (for example, x-y plane) image obtained by the surgical microscope unit and two-dimensional (for example, x-z plane) tomography images obtained by the OCT unit, and may further derive a three-dimensional (x-y-z) image according from the two-dimensional tomography images. Some or all of these images may be outputted (for example, displayed) by an output unit (for example, a display).

Specifically, the surgical microscope unit may achieve large-field two-dimensional (for example, x-y plane) imaging on the area to operate on, and output in real time, through the processor, the two-dimensional image of the area to operate on to the output unit for output.

The OCT unit may perform two-dimensional (for example, x-z plane) tomography imaging on the area to operate on according to the correspondence relationship between the fields calibrated in 402, and output the detected interference signal to the processor for processing.

The processor may reconstruct the imaging interference signal outputted by the OCT unit into a two-dimensional tomography image, and may derive, using an algorithm, a three-dimensional (x-y-z) image from a series of two-dimensional tomography images, and output the two-dimensional tomography images and/or the three-dimensional stereo image to the output unit for output.

Then, the method proceeds to 405. At 405, the OCT unit navigates the surgery.

For example, the OCT unit may perform two-dimensional tomography imaging on the area to operate on. In order to reduce scanning by the OCT unit, the scanning range of the OCT unit may be limited to the body part to operate on or a surrounding thereof, especially to a surrounding of the position of the surgical instrument. Thereby, the resultant current two-dimensional tomography image and/or three-dimensional image comprise/comprises the whole or a part of the surgical instrument. Then, the real-time position of the surgical instrument, especially the depth position, may be determined according to these images. The processor may output the two-dimensional tomography image and/or the three-dimensional image to the output unit for output. Due to those processes, the output on the output unit may be a dynamic image of the surgical instrument moving towards the body part to operate on.

Then, the method proceeds to 406. At 406, it is judged whether the surgical instrument arrives at the body part to be operate on, and if not, the method proceeds to 405; otherwise, the method proceeds to 407.

For example, an operator may judge whether the surgical instrument arrives at the body part according to the image output in 403 and the image output in 405.

At 407, the OCT unit completes location navigation, and the surgery is performed on the body part to operate on.

In the above embodiments, the operator artificially judges whether the surgical instrument arrives at the body part to operate on by observing the displayed images (or "navigation information") with his eyes. However, the present disclosure is not limited thereto.

In an example, the method may selectively comprise 404, at which expected position coordinates t(x, y, z) of the body part to operate on may be determined based on the images obtained in 403.

Specifically, the expected position coordinates t(x, y, z) of the body part to operate on may be determined by user input or image recognition, as described above. In general, the body part to operate on is not a single point, and instead, covers a certain area. Therefore, the expected position coordinates t(x,y,z) may cover a certain range, or preferably a part of or some points in the range. For example, the expected position coordinates t(x,y,z) may be inputted (for example, by touching as described above) by the operator to the processor, and the processor may convert the input into the unified coordinate system which has been established.

Further, as described above, initial position coordinates $t_0(x,y,0)$ of the surgical instrument may be determined by user input or image recognition (here for convenience of description, assume that the initial position of the surgical instrument is located on a surface of the tissue, and thus the depth is 0; of course, the present disclosure is not limited thereto). For example, the initial position coordinates $t_0(x, y,0)$ of the surgical instrument may be determined based on a two-dimensional (for example, x-y plane) image obtained by the surgical microscope unit. In an embodiment, the operator (for example, a surgeon) may place the surgical instrument in the range of the body part to operate on by observing at an exit pupil position of the surgical microscope unit. That is, "x" and "y" in the initial position coordinates $t_0(x,y,0)$ of the surgical instrument has already been kept to substantially correspond to "x" and "y" in the expected position coordinates t(x,y,z) of the body part to operate on. Thereby, basically it is only necessary for the surgical instrument to cut downward into the tissues.

The processor may mark the initial coordinates $t_0(x,y,0)$ of the surgical instrument and the expected position coordinates t(x,y,z) of the body part to operate on the three-dimensional (x-y-z) image obtained by the OCT unit, and output the image to the output unit for output.

In such a case, in the process of navigation in 405, current coordinates $t_1(x_1,y_1,z_1)$ of the surgical instrument may be determined by the two-dimensional tomography imaging in combination with, for example, image recognition. The processor may mark the current coordinates $t_1(x_1,y_1,z_1)$ of the surgical instrument on the three-dimensional (x-y-z) image obtained by the OCT unit, and output the image to the output unit for output.

In an example, a driving voltage for an x-scanning oscillator mirror of the OCT unit may be set to 0, to achieve y-z plane tomography imaging, and a tomography image may be reconstructed by the processor. Next, a driving voltage for a y-scanning oscillator mirror of the OCT unit may be set to 0, to achieve x-z plane tomography imaging, and a tomography image may be reconstructed by the processor. For example, a central field of the microscope unit may be approximately located at the accurate position of the body part to operate on. In addition, it is possible to ensure that the x-y field of the OCT unit corresponds to the central field of the microscope by the above calibration. Then, regardless of whether the voltage for the x-scanning oscillator mirror or the y-scanning oscillator mirror is set to 0, the central field can be located at the area to operate on, i.e., the position of the surgical instrument. The both imaging approaches may be performed at a fixed time interval. The time interval may be selected to achieve a sampling rate of several frames per second, thereby achieving substantially real-time imaging. The current coordinate position $t_1(x_1, y_1, z_1)$ of the surgical instrument is calculated based on y-z and x-z images in two consecutive frames.

In the above case where the expected position coordinates t(x,y,z) and the current coordinates $t_1(x_1,y_1,z_1)$ of the surgical instrument are determined, in 406, it may be judged by the processor whether the current position coordinates $t_1(x_1, y_1,z_1)$ coincide with the expected position coordinates t(x, y,z) through,for example, comparison. In addition, the processor may further output a navigation path on the output unit or output navigation information in a form of audio according to the comparison.

From the foregoing, it will be appreciated that specific embodiments of the disclosure have been described herein for purposes of illustration, but that various modifications may be made without deviating from the disclosure. In addition, many of the elements of one embodiment may be combined with other embodiments in addition to or in lieu of the elements of the other embodiments. Accordingly, the technology is not limited except as by the appended claims.

We claim:

1. A microscopic surgery system, comprising:
   an object lens;
   a surgical microscope unit configured to perform two-dimensional imaging on an area to operate on via the object lens;
   an optical coherence tomography unit configured to perform two-dimensional tomography imaging on the area to operate on via the object lens, wherein an imaging field of the optical coherence tomography unit is calibrated according to an imaging field of the surgical microscope unit;
   a processor configured to obtain navigation information based on the two-dimensional imaging by the surgical microscope unit and the two-dimensional tomography imaging by the optical coherence tomography unit, the navigation information comprising positional information of a body part to operate on and a surgical instrument for operating on the body part; and
   a guide configured to output the navigation information to guide the surgical instrument to the body part,
   wherein the processor is further configured to calibrate the imaging field of the optical coherence tomography unit by:
      establishing a unified coordinate s stem with a center of the imaging field of the surgical microscope unit as an origin and optical scanning lines of the optical coherence tomography unit as x, y, and z axes; and
      recording positions, in the coordinate system, of the x and y scanning lines of the optical coherence tomography unit driven under different scanning voltages and establishing a correspondence relationship between different driving voltages and scanning positions.

2. The microscopic surgery system according to claim 1, wherein the object lens comprises a microscopic object lens.

3. The microscopic surgery system according to claim 1, wherein the surgical microscope unit is configured to perform imaging via a paraxial area of the object lens, and the optical coherence tomography unit is configured to perform imaging via an on-axis area of the object lens.

4. The microscopic surgery system according to claim 1, wherein
   the navigation information comprises at least one of a two-dimensional image from the surgical microscope unit, a two-dimensional tomography image from the optical coherence tomography unit, or a three-dimensional image derived from the two-dimensional tomography image, and
   the guide comprises a display unit configured to display the navigation information.

5. The microscopic surgery system according to claim 4, wherein the processor is configured to highlight the body part to operate on and/or the surgical instrument on the displayed two-dimensional image and/or three-dimensional image.

6. A microscopic surgery navigation method, comprising:
   calibrating an imaging field of an optical coherence tomography unit according to an imaging field of a surgical microscope unit;
   performing, by the surgical microscope unit, two-dimensional imaging on an area to operate on via an object lens, and performing, by the optical coherence tomography unit, two-dimensional tomography imaging on the area to operate on via the object lens;
   obtaining navigation information based on results of the imaging, the navigation information comprising positional information of a body part to operate on and a surgical instrument for operating on the body part; and
   outputting the navigation information to guide the surgical instrument to the body part,
   wherein calibrating an imaging field of an optical coherence tomography unit comprises:
      establishing a unified coordinate system, with a center of the imaging field of the surgical microscope unit as an origin and optical scanning lines of the optical coherence tomography unit as x, y, and z axes; and
      recording positions, in the coordinate system, of the x and y scanning lines of the optical coherence tomography unit driven under different scanning voltages and establishing a correspondence relationship between different driving voltages and scanning positions.

7. The method according to claim 6, wherein
   the navigation information comprises at least one of a two-dimensional image from the surgical microscope unit, a two-dimensional tomography image from the optical coherence tomography unit, or a three-dimensional image derived from the two-dimensional tomography images, and
   outputting the navigation information comprises displaying the navigation information.

8. The method according to claim 7, further comprising:
   highlighting the body part to operate on and/or the surgical instrument on the displayed two-dimensional image and/or three-dimensional image.

9. The method according to claim 6, further comprising:
   performing y-z plane tomography imaging and x-z plane tomography imaging at a fixed time interval, and obtaining a current position of the surgical instrument based on a y-z tomography image and an x-z tomography image in two consecutive frames.

* * * * *

UNITED STATES PATENT AND TRADEMARK OFFICE
CERTIFICATE OF CORRECTION

| | |
|---|---|
| PATENT NO. | : 9,693,829 B2 |
| APPLICATION NO. | : 14/614703 |
| DATED | : July 4, 2017 |
| INVENTOR(S) | : Guohua Shi |

It is certified that error appears in the above-identified patent and that said Letters Patent is hereby corrected as shown below:

On the Title Page

Item [54], After "TOMOGRAPHY" delete "(OCT) AND AUTOMATED OCT IMAGING FIELD CALIBRATION".

In the Specification

Column 1 Lines 4-5, After "TOMOGRAPHY" delete "(OCT) AND AUTOMATED OCT IMAGING FIELD CALIBRATION".

Column 1 Line 48, Change "like,is" to --like, is--.

Column 1 Line 58, Change "techniques,such" to --techniques, such--.

Column 2 Lines 27-37, Delete "The navigation information may comprise at least one of a two-dimensional image from the surgical microscope unit, a two-dimensional tomography image of the OCT unit, or a three-dimensional image derived from the two-dimensional tomography image. In this case, the output unit may comprise a display unit configured to display the navigation information. The processor may be configured to highlight the body part to operate on and/or the surgical instrument on the displayed two-dimensional image and/or three-dimensional image." and insert the same on Column 2, Line 26, as a continuation of the same paragraph.

Column 2 Line 53, Change "system,with" to --system, with--.

Column 4 Line 22, Change "hand,the" to --hand, the--.

Column 6 Line 22, Change "embodiment,the" to --embodiment, the--.

Column 6 Line 45, Change "marksubstance" to --mark substance--.

Signed and Sealed this
Twelfth Day of February, 2019

Andrei Iancu
*Director of the United States Patent and Trademark Office*

CERTIFICATE OF CORRECTION (continued)
U.S. Pat. No. 9,693,829 B2

Column 7 Line 5, Change "1described" to --1 described--.

Column 7 Line 46, Change "207.The" to --207. The--.

Column 8 Line 22, Change "prisms,or" to --prisms, or--.

Column 11 Line 15, Change "through,for" to --through, for--.

In the Claims

Column 11 Line 51, Claim 1, change "s stem" to --system,--.